US010967019B2

(12) United States Patent
Cheng et al.

(10) Patent No.: US 10,967,019 B2
(45) Date of Patent: *Apr. 6, 2021

(54) METHOD FOR PROTECTING MITOCHONDRIA IN RETINA CELL

(71) Applicant: TAIWAN MITOCHONDRION APPLIED TECHNOLOGY CO.,LTD., Zhubei, Hsinchu County (TW)

(72) Inventors: Han-Chung Cheng, Zhubei (TW); Chi-Tang Tu, Zhubei (TW); Shun-Chieh Yang, Zhubei (TW); Man-Ching Shen, Zhubei (TW)

(73) Assignee: TAIWAN MITOCHONDRION APPLIED TECHNOLOGY CO., LTD., Zhubei (TW)

( * ) Notice: Subject to any disclaimer, the term of this patent is extended or adjusted under 35 U.S.C. 154(b) by 558 days.

This patent is subject to a terminal disclaimer.

(21) Appl. No.: 15/715,056

(22) Filed: Sep. 25, 2017

(65) Prior Publication Data

US 2018/0008657 A1 Jan. 11, 2018

Related U.S. Application Data

(63) Continuation-in-part of application No. 15/364,235, filed on Nov. 29, 2016, now Pat. No. 10,213,467.

(30) Foreign Application Priority Data

Nov. 30, 2015 (TW) .............................. 104139891 A
Sep. 26, 2016 (TW) .............................. 105131040 A (51) Int. Cl.
| | |
|---|---|
| *A61K 36/185* | (2006.01) |
| *A61K 9/00* | (2006.01) |
| *A61K 9/08* | (2006.01) |
| *A61K 36/47* | (2006.01) |
| *A61K 9/48* | (2006.01) |

(52) U.S. Cl.
CPC .......... *A61K 36/185* (2013.01); *A61K 9/0053* (2013.01); *A61K 9/08* (2013.01); *A61K 36/47* (2013.01); *A61K 9/4875* (2013.01)

(58) Field of Classification Search
None
See application file for complete search history.

(56) References Cited

U.S. PATENT DOCUMENTS

| | | | |
|---|---|---|---|
| 6,235,721 B1 | 5/2001 | Ghosal | |
| 2005/0130878 A1 | 6/2005 | Roque et al. | |
| 2012/0107432 A1* | 5/2012 | Antony | .................. A61K 36/47 |
| | | | 424/769 |
| 2013/0137728 A1 | 5/2013 | Beeson et al. | |

FOREIGN PATENT DOCUMENTS

| | | |
|---|---|---|
| JP | 2009-190988 A | 8/2009 |
| JP | 2010-178627 A | 8/2010 |
| JP | 2012-527404 A | 11/2012 |
| WO | 2010/134206 A1 | 11/2010 |
| WO | 2013/022788 A1 | 2/2013 |

OTHER PUBLICATIONS

Raskin et al. (2004) Current Pharmaceutical Design, 10, 3419-3429. (Year: 2004).*
Revilla et al. (1998) J. Agric. Food Chem. 46, 4592-4597. (Year: 1998).*

* cited by examiner

*Primary Examiner* — Russell G Fiebig
(74) *Attorney, Agent, or Firm* — Maschoff Brennan (57) ABSTRACT

A use of an emblica extract in preparing a pharmaceutical composition for protecting mitochondria in retina is provided. When the pharmaceutical composition, which comprises the emblica extract, is provided to retinal cells, a use of the pharmaceutical composition comprises improvement of the ability of performing the oxidative phosphorylation for the synthesis of the adenosine triphosphate (ATP) by the mitochondria in the retinal cells under or exposed to ultraviolet light, and improvement of the coupling efficiency of the synthesis of the adenosine triphosphate by the mitochondria.

14 Claims, 10 Drawing Sheets

METHOD FOR PROTECTING MITOCHONDRIA IN RETINA CELL

CROSS-REFERENCE TO RELATED APPLICATIONS

This application is a continuation in part application of U.S. patent application Ser. No. 15/364,235 filed on Nov. 29, 2016, entitled "METHOD FOR IMPROVING MITOCHONDRIA AND METHOD FOR PROMOTING CELL DIVISION OF STEM CELL", which claims priority under 35 U.S.C. § 119(a) on Patent Application No(s). 104139891 filed in Taiwan, R.O.C. on Nov. 30, 2015, this application also claims priority under 35 U.S.C. § 119(a) on Patent Application No(s). 105131040 filed in Taiwan, R.O.C. on Sep. 26, 2016, the entire contents of which are hereby incorporated by reference.

TECHNICAL FIELD

The present disclosure relates to a use of preparing a pharmaceutical composition for protecting mitochondria in retina, more particularly to a use of an emblica extract in preparing a pharmaceutical composition for protecting mitochondria in retina.

BACKGROUND

Mitochondria (called "mitochondrion" in singular form) are places where oxidative phosphorylation (OXPHOS) and adenosine triphosphate (ATP) synthesis occur. Since ATP is used as a source of energy in a cell, the mitochondria are described as the powerhouse of the cell. In addition to generating energy required by the cell, the mitochondria also participate in cell division, cell signaling and apoptosis of the cell, and the mitochondria has the ability to control the cell-division cycle.

Eyes are commonly called as the windows of the soul, and the retina in eyes converts light into visual signals. The retina is composed of several different kinds of cells, and retinal cells are the most essential one. The mitochondria in the retinal cells provide energy to the retinal cells, including the energy required for the retinal cells to convert light into visual signals.

SUMMARY

According to one aspect of the present disclosure, a use of an emblica extract in preparing a pharmaceutical composition for protecting mitochondria in retina is provided. When the pharmaceutical composition, which comprises the emblica extract, is provided to retinal cells, a use of the pharmaceutical composition comprises improvement of the ability of performing the oxidative phosphorylation for the synthesis of the adenosine triphosphate (ATP) by the mitochondria in the retinal cells under or exposed to ultraviolet light, and improvement of the coupling efficiency of the synthesis of the adenosine triphosphate by the mitochondria.

BRIEF DESCRIPTION OF THE DRAWINGS

The present disclosure will become more fully understood from the detailed description given hereinbelow and the accompanying drawings which are given by way of illustration only and thus are not intending to limit the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

*Emblica officinalis*, also known as Phyllanthus emblica, Emblic, Emblic myrobalan, Myrobalan, Indian gooseberry, Malacca tree, or Amla from Sanskrit amalika, is a deciduous tree of the family Phyllanthaceae, and it is known for its edible fruit of the same name. Emblica emblica is native to India and distributed to South China and Malaysia.

The present disclosure discloses an emblica extract. In some embodiments, the emblica extract is obtained from the fruit of *Emblica officinalis* by supercritical fluid extraction, and carbon dioxide is usually used as the supercritical fluid. In some embodiments, an aqueous salt solution such as a 0.1 to 5% (w/w) of sodium chloride, potassium chloride, calcium chloride or magnesium chloride solution, methanol, ethanol, acetone and ethyl acetate is used to extract the fruit of *Emblica officinalis* to obtain an initial extract; after that, the initial extract is filtered and purified to obtain the emblica extract. The emblica extract can be processed into powder form by spray drying or vacuum drying for easier preservation.

In some embodiments, the emblica extract comprises 35-55 wt % of a mixture of Emblicanin-A and Emblicanin-B, 4-15 wt % of Punigluconin, 10-20 wt % of Pedunculagin, 5-15 wt % of Rutin and 10-30 wt % of Gallo-ellagitannoids.

The emblica extract has multiple characteristic infrared absorption peaks at 3403.6±5 cm$^{-1}$, 2931.6±5 cm$^{-1}$, 1385.0±5 cm$^{-1}$, 1318.6±5 cm$^{-1}$, 1623.5±5 cm$^{-1}$, 1451.3±5 cm$^{-1}$, 1352.1±5 cm$^{-1}$ 1218.4±5 cm$^{-1}$, 1148.6±5 cm$^{-1}$, 1035.7±5 cm$^{-1}$ and 3403.6±5 cm$^{-1}$, respectively. The emblica extract has multiple characteristic peaks on a high-performance liquid chromatogram at retention time of 1.620±0.5 min, 2.148±0.5 min, 3.265±0.5 min and 4.370±0.5 min, respectively.

The structural formula of Emblicanin-A, also named 2,3-di-O-galloyl-4,6-(S)-hexahydroxydiphenoyl-2-keto-glucono-lactone, is:

The structural formula of Emblicanin-B, also named 2,3,4,6-bis-(S)-hexahydroxydiphenoyl-2-keto-glucono-lactone, is:

The structural formula of Punigluconin, also named 2,3-di-O-galloyl-4,6-(S)-hexahydroxydiphenoyl gluconic acid, is:

The structural formula of Pedunculagin, also named 2,3,4,6-bis-(S)-hexahydroxydiphenoyl-D-glucose, is:

The structural formula of Rutin, also named 3',4',5,7-tetrahydroxyflavono-1,3-O-rhamnoglucoside, is:

In some embodiments, when an aqueous solution of the emblica extract with a mass concentration from 250 to 500 µg/ml is provided to retinal cells, the emblica extract, which enters into the retinal cells and then into the mitochondria, is able to protect the inner membranes of the mitochondria. Therefore, after the retinal cells are exposed to ultraviolet light, the efficiency of performing the oxidative phosphorylation for the synthesis of the adenosine triphosphate (ATP) in the inner membranes of the mitochondria is not significantly decreased. In detail, when the mitochondria in the retinal cells are protected by the emblica extract, the yield of ATP in the mitochondria is not significantly decreased, a proton leakage in the inner membranes of the mitochondria is not significantly increased, and the coupling efficiency of ATP synthesis in the mitochondria during the oxidative phosphorylation is not significantly decreased. When the inner membranes of the mitochondria in the retinal cells are protected by the emblica extract, the mitochondrial breakdown is postponed, thereby slowing down apoptosis of the retinal cells caused by the mitochondrial breakdown.

In some embodiments, the emblica extract or the pharmaceutical composition including the emblica extract is provided in an oral dosage form (oral administration); that is, a person is able to treat the retinal cells in the body by eating or drinking the emblica extract or the pharmaceutical composition. When the emblica extract or the pharmaceutical composition is provided by oral administration, the effective dose of the emblica extract is from 60.75 mg to 121.5 mg. The effective dose in human is obtained according to a conversion equation. The conversion equation is: (effective dose in human)=(effective dose in cell experiment)×(body weight of mice)×(conversion coefficient)×(body weight of human). The conversion coefficient is obtained from the conversion coefficient table. For example, when the body weight of mice is 20 kg and the body weight of human is 60 kg, the conversion coefficient is 0.081.

To make the oral administration more convenient, the emblica extract or the pharmaceutical composition including the emblica extract is able to be made into a processed food in liquid form, solid form, powder form, granular form, paste form or colloidal form. An excipient or a flavor enhancer can be added into the processed food for better flavor and convenient administration.

The excipient is, for example, wheat starch, rice starch, corn starch, potato starch, dextrin, cyclodextrin, lactose, glucose, sugar, reduced maltose, cerealose, oligofructose, galactooligosaccharide, sorbitol, erythritol, xylitol, lactitol, or mannitol.

The flavor enhancer is, for example, longan extract, lychee extract, grapefruit extract, apple juice, orange juice, lemon juice, peach essence, plum essence, yogurt essence, acesulfame potassium, sucralose, erythritol, oligosaccharide, mannose, xylitol, isomerized sugar, citric acid, malic acid, tartaric acid, gluconate, green tea, oolong tea, banaba tea, eucommia tea, tieguanyin tea, coix tea, jiaogulan tea, zizania latifolia tea, or kelp tea.

Moreover, the emblica extract or the pharmaceutical composition including the emblica extract may be encapsulated in a capsule for convenient oral administration. The emblica extract or the pharmaceutical composition including the emblica extract may be encapsulated in a hard capsule in a dried powder form. Also, the emblica extract or the pharmaceutical composition including the emblica extract may be in a liquid form, suspension form, paste form, powder form or granular form encapsulated in a soft capsule.

The oil in the soft capsule for dissolving the emblica extract is, for example, avocado oil, almond oil, flaxseed oil, fennel oil, *Perilla frutescens* oil, olive oil, olive squalene, sweet orange oil, orange roughy oil, sesame oil, garlic oil, cocoa butter, pumpkin seed oil, chamomile oil, carrot oil, cucumber oil, tallow fatty acid, kukui nut oil, lingonberry seed oil, brown rice germ oil, rice bran oil, wheat germ oil, safflower oil, shea butter, liquid shea butter, perilla oil, soybean oil, evening primrose oil, camellia oil, corn oil, rapeseed oil, saw palmetto extract oil, coix oil, peach kernel oil, celery seed oil, castor oil, sunflower oil, grapeseed oil, borage oil, macadamia nut oil, meadowfoam oil, cottonseed oil, peanut oil, turtle oil, mink oil, egg yolk oil, fish oil, palm oil, palm-kernel oil, wood wax oil, coconut oil, long-chain/medium-chain/short-chain triglyceride, diglyceride, butter, lard, squalene, squalane and pristane and hydrides thereof. In addition, both borage oil and evening primrose oil contain a great amount of gamma-linolenic acid which is an essential fatty acid for human body. Gamma-linolenic acid is favorable for retaining skin moisture, stimulating cell regeneration and increasing the activity of brown fat to burn fat.

In some embodiments, several food additives approved for use, such as colorant, preservative, tackifier, binder, disintegrant, dispersant, stabilizer, gelatinizer, antioxidant, surfactant and pH control agent, are added into the processed food.

According to the present disclosure, there are two embodiments of the present disclosure, one comparative embodiment and one control group depicted as below, for describing the use of the emblica extract in preparing the pharmaceutical composition for protecting the mitochondria in the retina. Several experimental data are summarized for describing the effect of the use.

According to the present disclosure, the emblica extract is derived by the following steps: first, soaking the fruit of *Emblica officinalis* with an aqueous solution of sodium chloride having a concentration of 1% (w/w); second, heating the aqueous solution at a temperature of between 65° C. to 75° C. for 1 hour on a steam bath; third, filtering the aqueous solution to obtain a filtered extract; fourth, freezing the filtered extract for 3 days; fifth, spray drying the filtered extract to obtain a powdered emblica extract, and the powdered emblica extract is brown colored powder. The emblica extract includes 27 wt % of Emblicanin-A, 23 wt % of Emblicanin-B, 8 wt % of Punigluconin, 14 wt % of Pedunculagin, 10 wt % of Rutin and 10-30 wt % of Galloellagitannoids. According to the present disclosure, the emblica extract is not limited to be the extract of *Emblica officinalis*. Other emblica extracts known by different scientific names while having similar composition would be applicable to the present disclosure.

Figure 1:
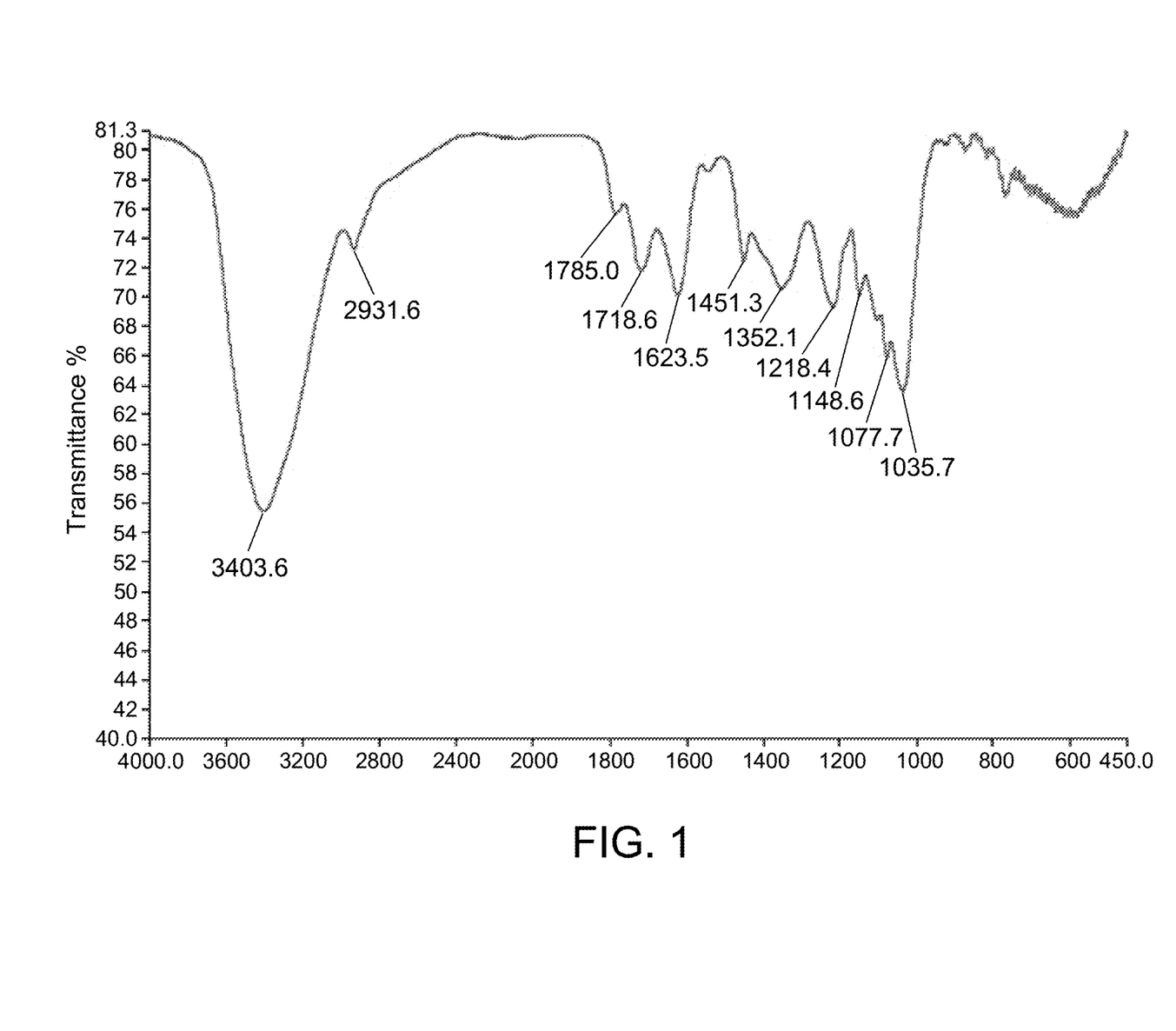
FIG. 1 is an infrared absorption spectrum of an emblica extract in a first embodiment and a second embodiment.
Figure 2:
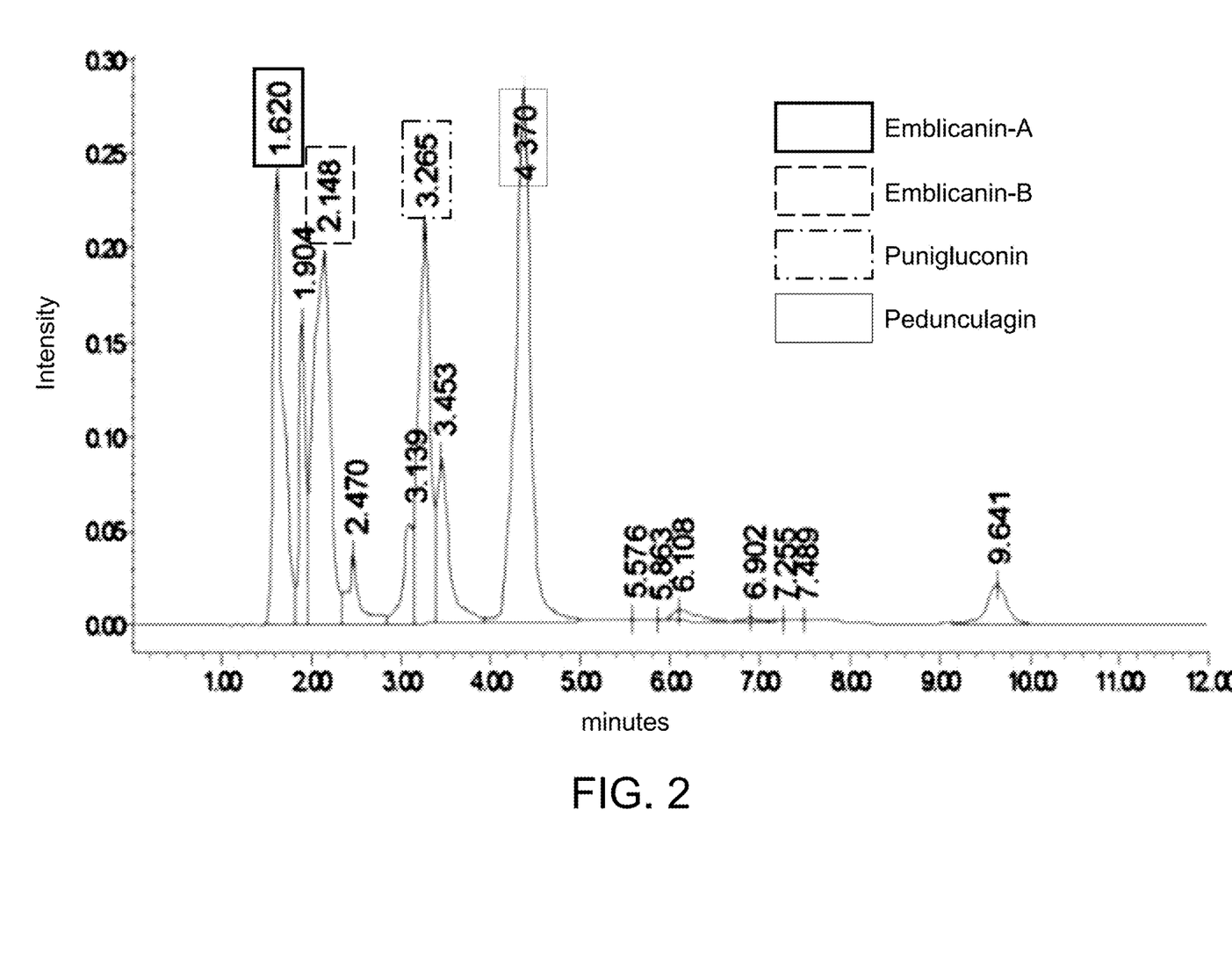
FIG. 2 is a high-performance liquid chromatogram of the first embodiment and the second embodiment.

Please refer to FIG. 1 and FIG. 2. FIG. 1 is an infrared absorption spectrum of an emblica extract in a first embodiment and a second embodiment. FIG. 2 is a high-performance liquid chromatogram of the first embodiment and the second embodiment. As shown in FIG. 1, the emblica extract has multiple characteristic infrared absorption peaks at 3403.6 $cm^{-1}$, 2931.6 $cm^{-1}$, 1385.0 $cm^{-1}$, 1318.6 $cm^{-1}$, 1623.5 $cm^{-1}$, 1451.3 $cm^{-1}$, 1352.1 $cm^{-1}$, 1218.4 $cm^{-1}$, 1148.6 $cm^{-1}$, 1035.7 $cm^{-1}$ and 3403.6 $cm^{-1}$, respectively. As shown in FIG. 2, the emblica extract has multiple characteristic peaks on a high-performance liquid chromatogram at retention time of 1.620 min, 2.148 min, 3.265 min and 4.370 min, respectively.

The following embodiments are performed by using retinal cells (ARPE-19). A preparation for an experimental sample is to seed a total of 20,000 retinal cells in each well of a 24-well cell culture plate, and then incubate the retinal cells with a culture medium for 24 hours.

A simulation of damage to the retinal cells is performed by exposing the retinal cells to ultraviolet light within a wavelength of 365 nm.

In some experiments, an aqueous solution including the emblica extract with a predetermined mass concentration is added into the wells of the cell culture plate where the retinal cells are located without culture medium, and the retinal cells in the wells are incubated with the emblica extract for 24 hours. Next, the aqueous solution is removed from the wells, and then the retinal cells are exposed to ultraviolet light within a wavelength of 365 nm for a predetermined period of time. Next, the oxygen consumption rate of the retinal cells in the cell culture plate is measured by a Seahorse XF analyzer.

In the first embodiment, the aqueous solution of the emblica extract has a mass concentration of 250 μg/ml. In the second embodiment, the aqueous solution of the emblica extract has a mass concentration of 500 μg/ml. In the control group and the comparative embodiment, there is no aqueous solution of the emblica extract in the wells of the cell culture plate. In the control group, the retinal cells are not exposed to ultraviolet light.

The Seahorse XF analyzer measures the oxygen consumption rate of the retinal cells by the following steps: first, detecting the basal respiration in the retinal cells; second, adding some ATP synthesis inhibitors (e.g. Oligomycin) to decrease the activity of the mitochondria to synthesize ATP, and the reduction of the oxygen consumption rate is equal to the oxygen consumption rate of the oxidative phosphorylation for ATP synthesis (that is the basal respiration in the mitochondria); third, adding some anti-couplers (e.g., Carbonyl cyanide-4-(trifluoromethoxy)phenylhydrazone (FCCP)) in a proper mass concentration, which causes no damage to the electron transport chain in the inner mitochondrial membrane, to disrupt ATP synthesis, and evaluating the maximal respiration in the mitochondria; fourth, adding some electron transport chain inhibitors (e.g., a combination of Rotenone and Antimycin A) to totally stop the respiration in the mitochondria, and a measured background value is equal to the non-mitochondrial respiration.

Some parameters are obtained by the following formulas:

the basal respiration in the mitochondria=(the basal respiration in the retinal cells)−(the non-mitochondrial respiration);

the oxygen consumption rate required to compensate for proton leakage=(the basal respiration in the mitochondria)−(the oxygen consumption rate for ATP synthesis);

the spare respiratory capacity in the mitochondria=(the maximal respiration in the mitochondria)−(the basal respiration in the mitochondria); and the coupling efficiency of the synthesis of the adenosine triphosphate in the mitochondria=(the oxygen consumption rate for ATP synthesis)/(the basal respiration in the mitochondria).

Figure 3:
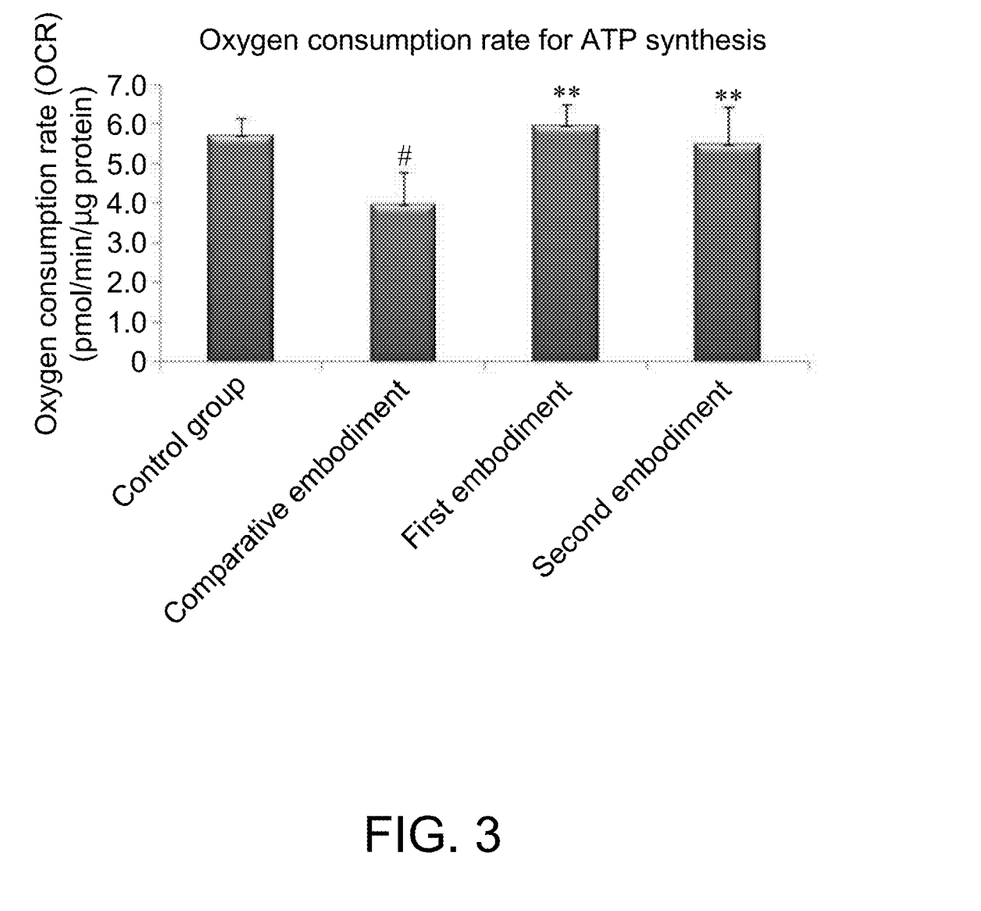
FIG. 3 is a bar chart presenting oxygen consumption rate for ATP synthesis of the first embodiment, the second embodiment, a comparative embodiment and a control group.
Figure 4:
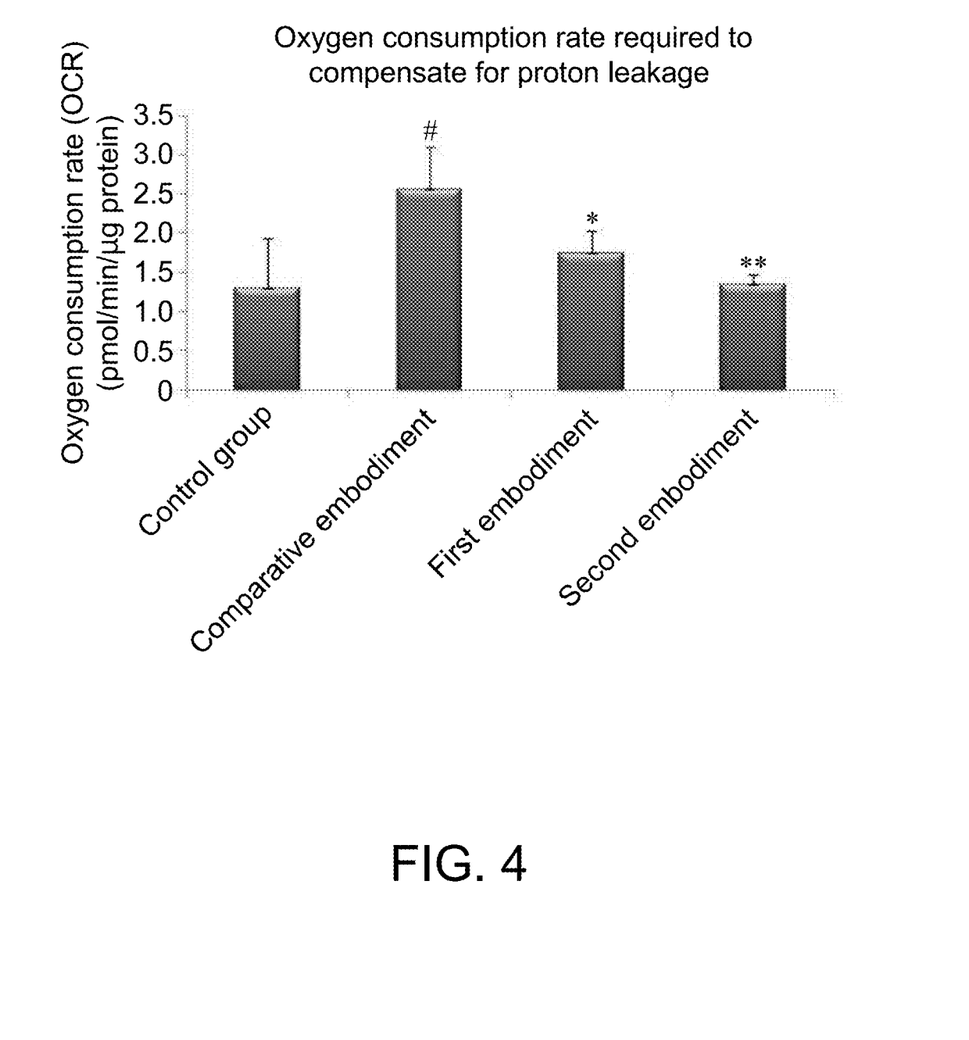
FIG. 4 is a bar chart presenting oxygen consumption rate required to compensate for proton leakage of the first embodiment, the second embodiment, the comparative embodiment and the control group.
Figure 5:
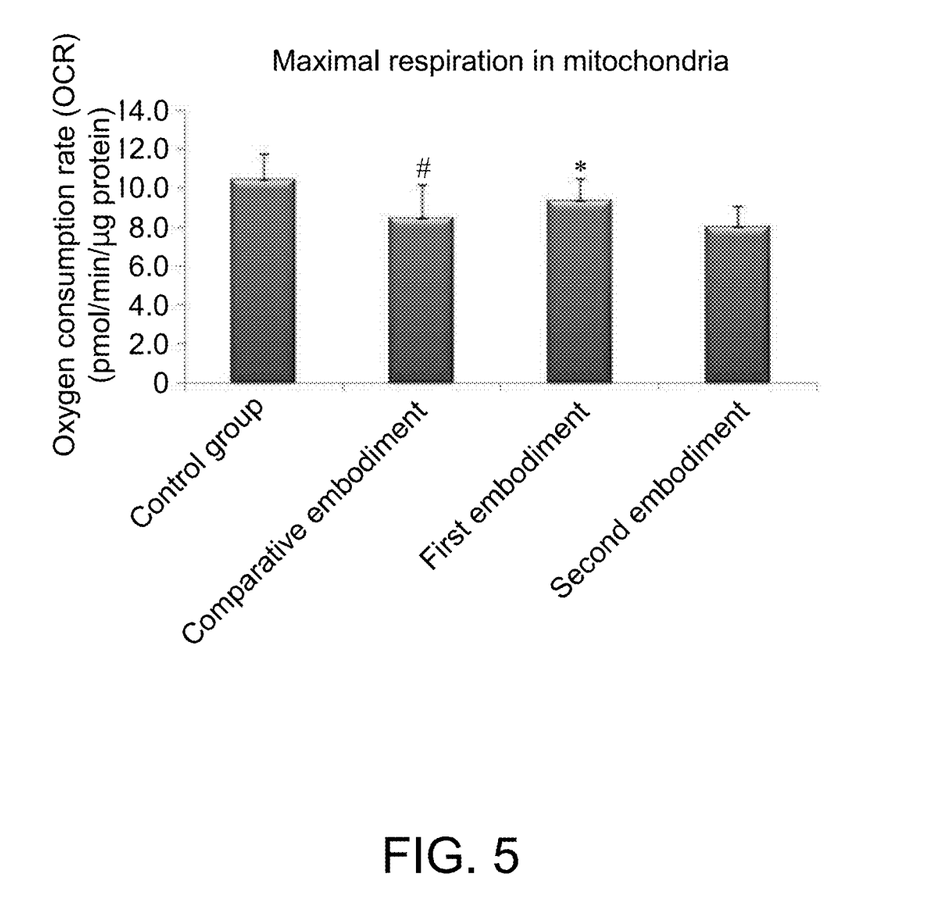
FIG. 5 is a bar chart presenting maximal respiration in mitochondria of the first embodiment, the second embodiment, the comparative embodiment and the control group.
Figure 6:
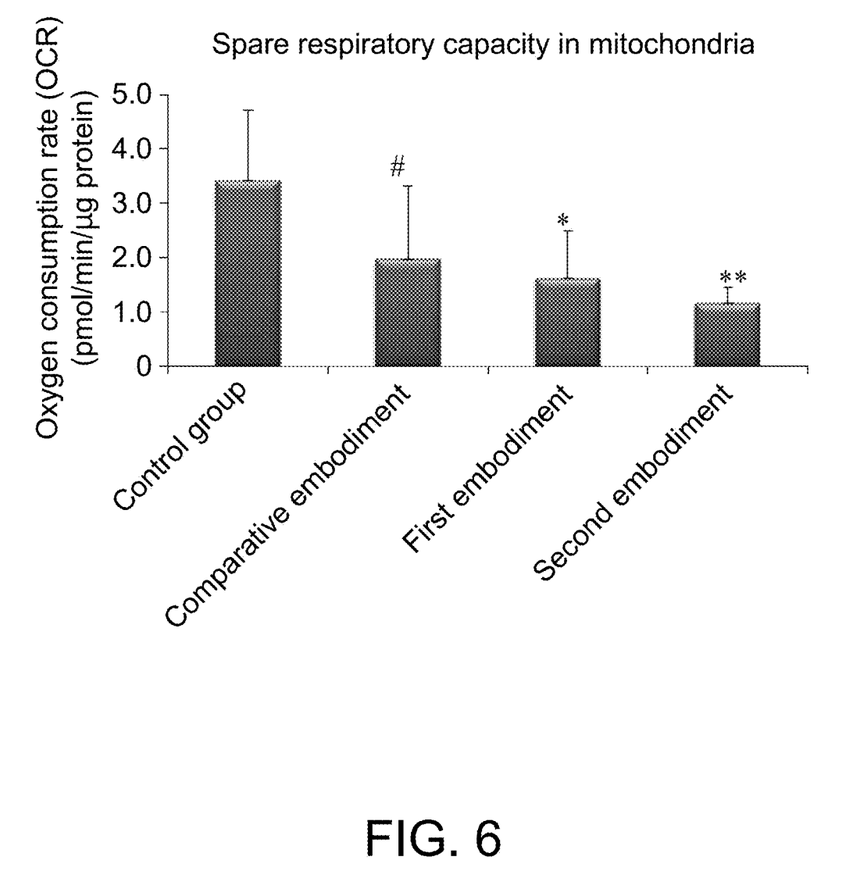
FIG. 6 is a bar chart presenting spare respiratory capacity in mitochondria of the first embodiment, the second embodiment, the comparative embodiment and the control group.
Figure 7:
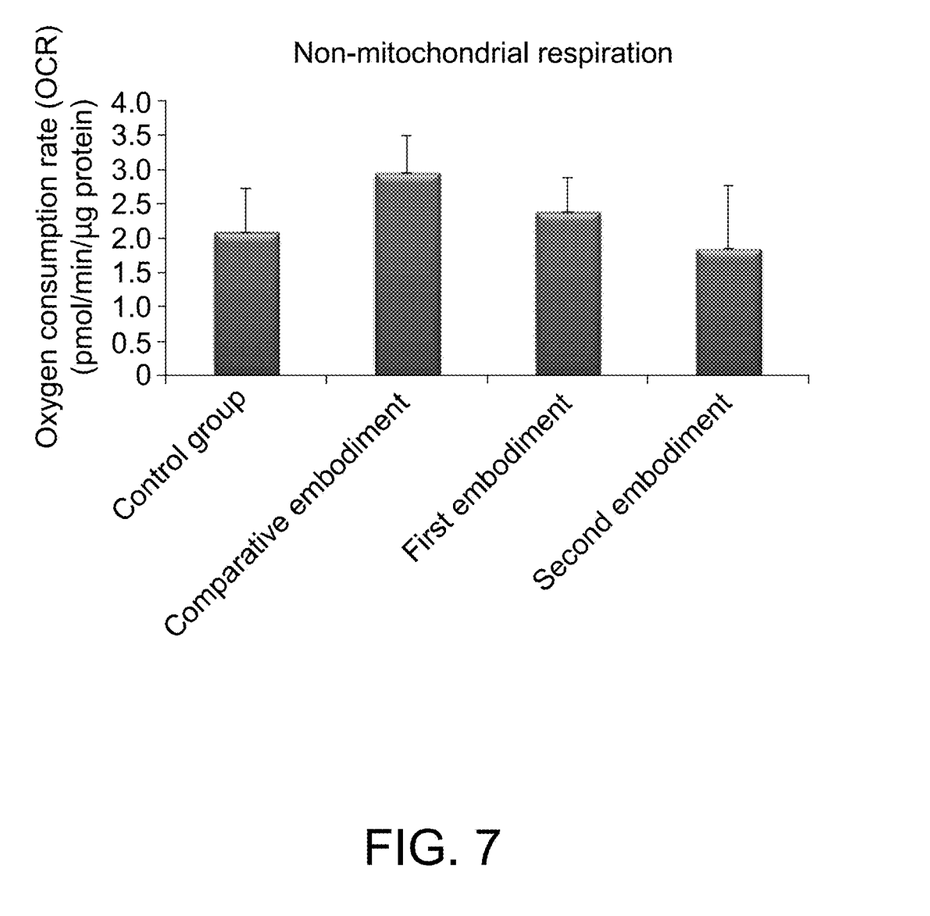
FIG. 7 is a bar chart presenting non-mitochondrial respiration of the first embodiment, the second embodiment, the comparative embodiment and the control group.
Figure 8:
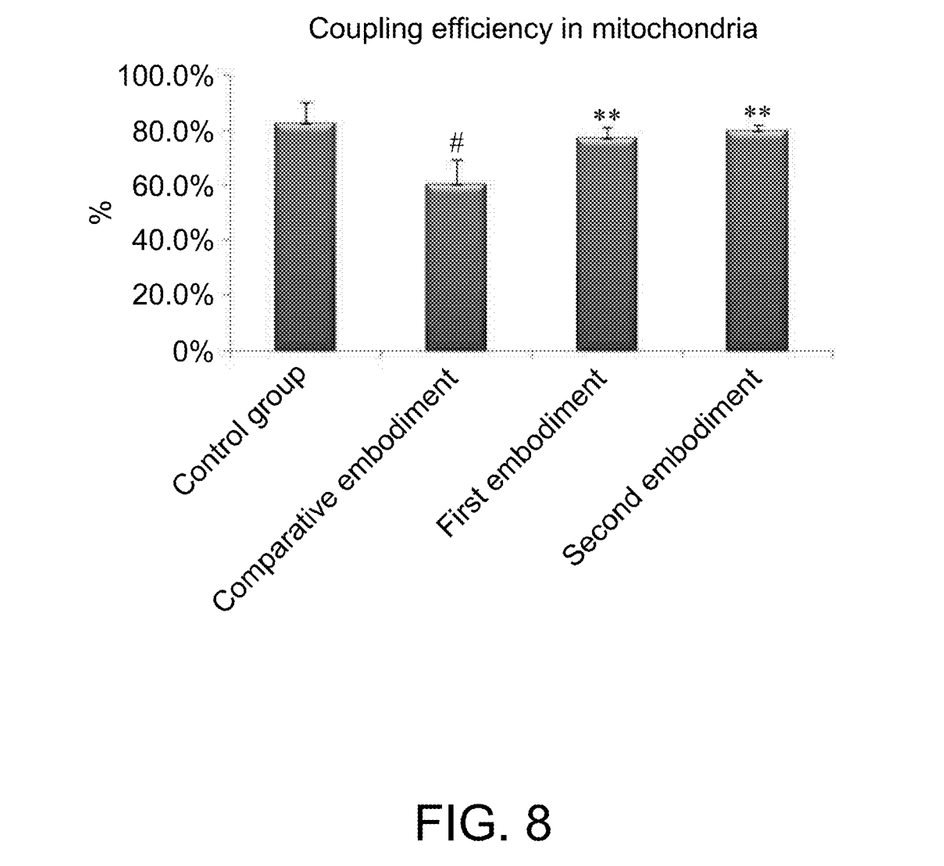
FIG. 8 is a bar chart presenting coupling efficiency in mitochondria of the first embodiment, the second embodiment, the comparative embodiment and the control group.
Figure 9:
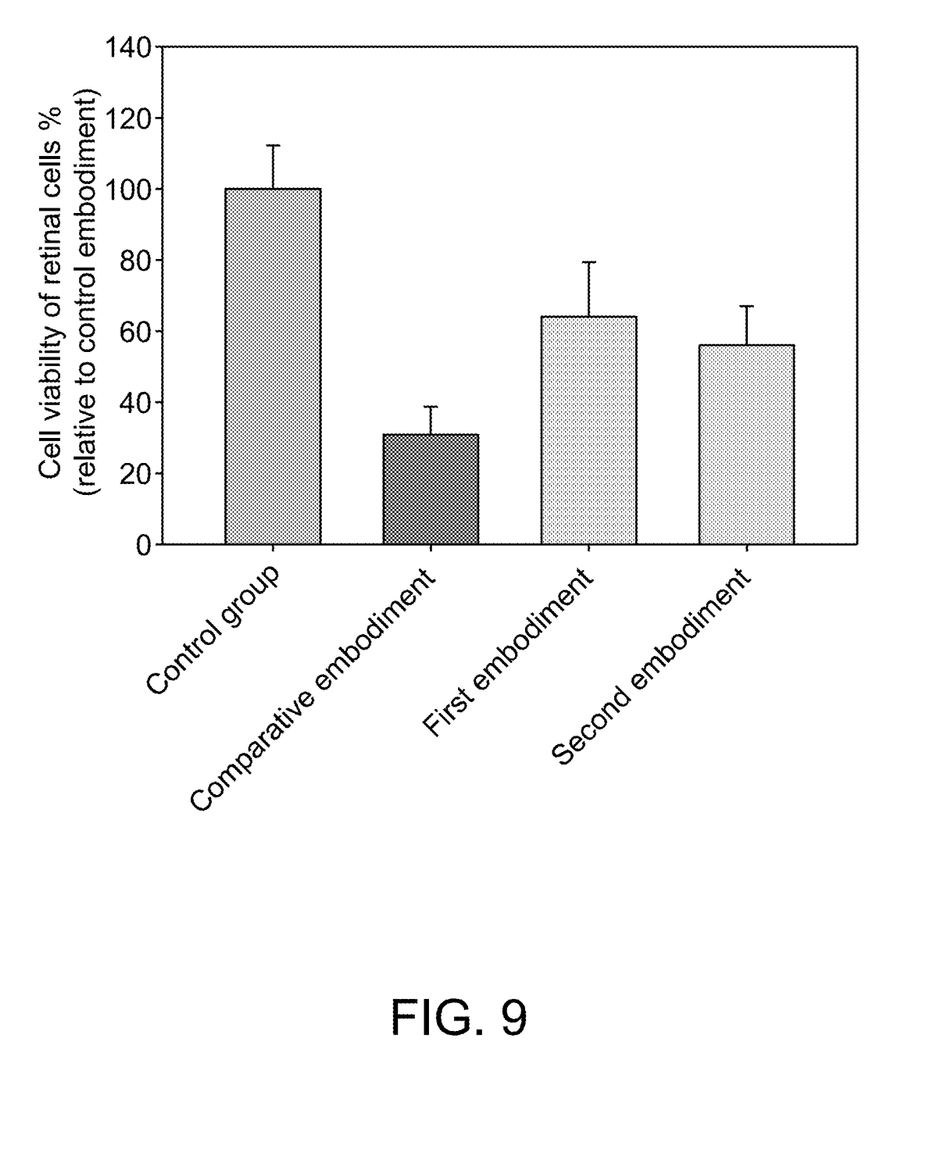
FIG. 9 is a bar chart presenting cell viability of retinal cells of the first embodiment, the second embodiment, the comparative embodiment and the control group, after the retinal cells are exposed to ultraviolet light.
Figure 10:
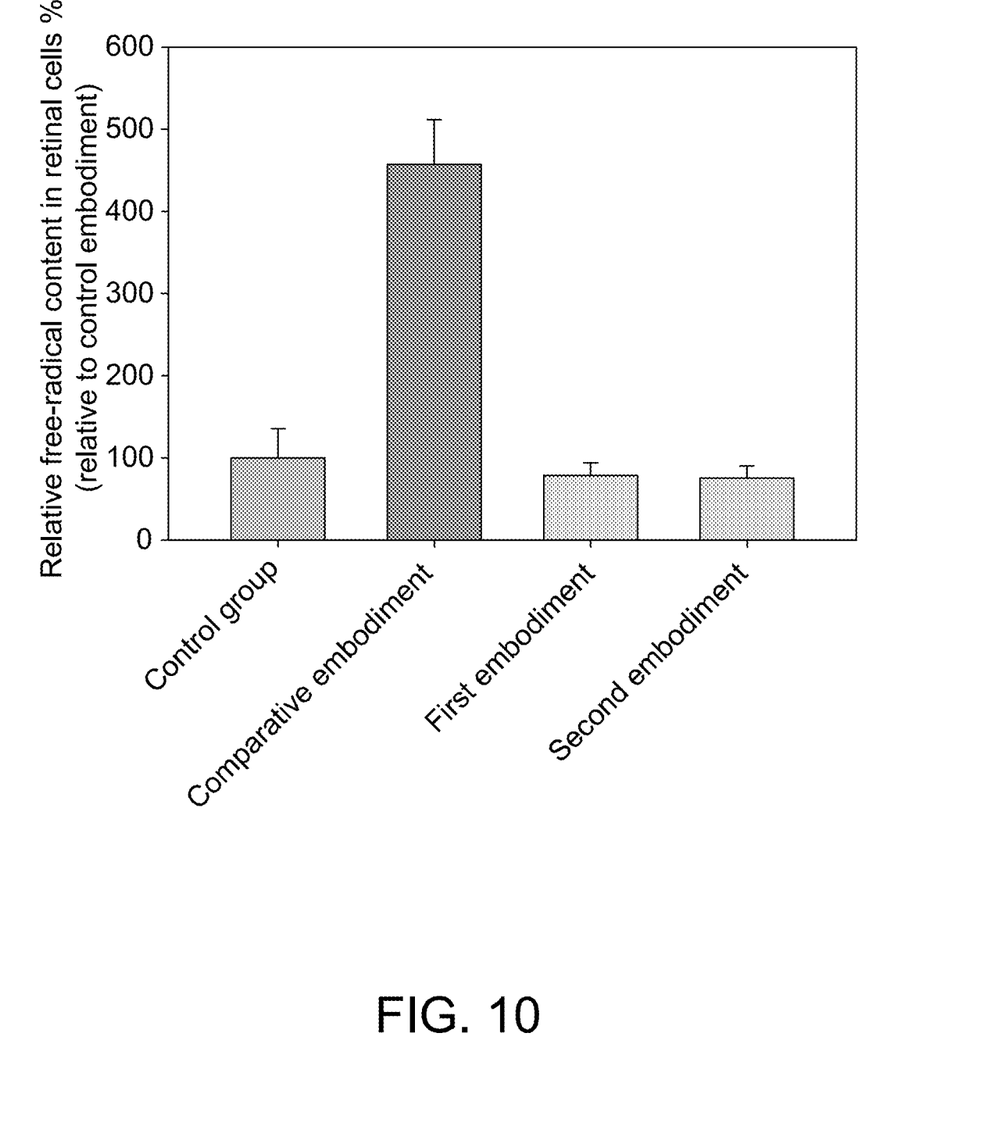
FIG. 10 is a bar chart presenting relative free-radical content in the retinal cells of the first embodiment, the second embodiment, the comparative embodiment and the control group, after the retinal cells are exposed to ultraviolet light.

The detailed experimental data of the two embodiments of the present disclosure, the comparative embodiment and the control group is shown in Table 1 below and FIG. 1 to FIG. 8. The experimental data of oxygen consumption rate (pmol/min) per μg protein shown in Table 1 is normalized by the quantity of the retinal cells. FIG. 3 is a bar chart presenting oxygen consumption rate for ATP synthesis of the first embodiment, the second embodiment, a comparative embodiment and a control group. FIG. 4 is a bar chart presenting oxygen consumption rate required to compensate for proton leakage of the first embodiment, the second embodiment, the comparative embodiment and the control group. FIG. 5 is a bar chart presenting maximal respiration in mitochondria of the first embodiment, the second embodiment, the comparative embodiment and the control group. FIG. 6 is a bar chart presenting spare respiratory capacity in mitochondria of the first embodiment, the second embodiment, the comparative embodiment and the control group. FIG. 7 is a bar chart presenting non-mitochondrial respiration of the first embodiment, the second embodiment, the comparative embodiment and the control group. FIG. 8 is a bar chart presenting coupling efficiency in mitochondria of the first embodiment, the second embodiment, the comparative embodiment and the control group. FIG. 9 is a bar chart presenting cell viability of retinal cells of the first embodiment, the second embodiment, the comparative embodiment and the control group, after the retinal cells are exposed to ultraviolet light. FIG. 10 is a bar chart presenting relative free-radical content in the retinal cells of the first embodiment, the second embodiment, the comparative embodiment and the control group, after the retinal cells are exposed to ultraviolet light.

TABLE 1

| | Mass concentration of emblica extract in solution (μg/ml) | Oxygen consumption rate for ATP synthesis | Oxygen consumption rate required to compensate for proton leakage | Maximal respiration in mitochondria |
|---|---|---|---|---|
| | | Exposed to UV light for 1 hour (pmol/min/μg protein) | | |
| First embodiment | 250 | 5.9 | 1.7 | 9.1 |
| Second embodiment | 500 | 5.5 | 1.5 | 7.9 |
| Comparative embodiment | 0 | 3.9 | 2.5 | 8.2 |
| Control Group | 0 | Without being exposed to ultraviolet light | | |
| | | 5.8 | 1.2 | 10.2 |

| | Spare respiratory capacity in mitochondria | Non-mitochondrial respiration | Coupling efficiency in mitochondria | Relative free-radical content in retinal cells Exposed to UV light for 2 hours | Cell viability of retinal cells Exposed to UV light for 4 hours |
|---|---|---|---|---|---|
| | Exposed to UV light for 1 hour | | | | |
| | (pmol/min/μg protein) | | % | % (relative to control group) | |
| First embodiment | 1.6 | 2.4 | 77 | 78 | 64 |
| Second embodiment | 1.2 | 1.8 | 79 | 75 | 56 |
| Comparative embodiment | 2.0 | 2.9 | 59 | 457 | 30 |
| Control Group | Without being exposed to ultraviolet light | | | | |
| | 3.4 | 2.1 | 82 | 100 | 100 |

As shown in FIG. 3, the oxygen consumption rate for ATP synthesis in the comparative embodiment is significantly lower than that in the control group (p<0.05). Furthermore, the oxygen consumption rate for ATP synthesis in the first embodiment and that in the second embodiment are similar to that in the control group. The oxygen consumption rate for ATP synthesis in the first embodiment is significantly higher than that in the comparative embodiment (p<0.01), and the oxygen consumption rate for ATP synthesis in the second embodiment is significantly higher than that in the comparative embodiment (p<0.01).

As shown in FIG. 4, the oxygen consumption rate required to compensate for the proton leakage in the comparative embodiment is significantly higher than that in the control group (p<0.05). Furthermore, the oxygen consumption rate required to compensate for the proton leakage in the first embodiment and that in the second embodiment are slightly higher than that in the control group. The oxygen consumption rate required to compensate for the proton leakage in the first embodiment is significantly lower than that in the control group (p<0.05), and the oxygen consumption rate required to compensate for the proton leakage in the second embodiment is significantly lower than that in the comparative embodiment (p<0.01).

As shown in FIG. 5, the maximal respiration in the mitochondria in the first embodiment is lower than that in the control group, but the maximal respiration in the mitochondria in the first embodiment is significantly higher than that in the comparative embodiment (p<0.05).

As shown in FIG. 6, the spare respiratory capacity in the first embodiment and that in the second embodiment are lower than that in the control group and comparative embodiment. As shown in FIG. 7 the non-mitochondrial respiration in the first embodiment and that in the second embodiment are lower than that in the comparative embodiment. As shown in FIG. 8, the coupling efficiency in the mitochondria in the first embodiment and that in the second embodiment are similar to that in the control group, and are significantly higher than that in the comparative embodiment.

According to the results shown in FIG. 3 to FIG. 5 and FIG. 8, the oxygen consumption rate required to compensate for the proton leakage in the first embodiment and that in the second embodiment are not significantly increased, compared to that in the comparative embodiment, which indicates that there is no severe damage to the inner mitochondrial membranes, thereby preventing massive proton leakage. Therefore, the oxygen consumption for re-transporting protons to the intermembrane space is reduced, such that the oxygen consumption rate for ATP synthesis and the coupling efficiency in the mitochondria are similar to that in the control group.

According to the aforementioned experimental data, the mitochondria, treated with the aqueous solution of the emblica extract having the mass concentration of 250 μg/ml to 500 μg/ml, are protected, and thereby the damage to the inner membranes of the mitochondria in the retinal cells exposed to ultraviolet light is reduced. Accordingly, the aqueous solution of the emblica extract having the mass concentration of 250 μg/ml to 500 μg/ml has the effect of protecting the mitochondria in the retinal cells, such that the time of occurring mitochondrial breakdown is postponed.

Moreover, as shown in FIG. 9, the cell viability of the retinal cells exposed to ultraviolet light in the first and second embodiments is less than that in the control group, and is significantly higher than that in the comparative embodiment. As shown in FIG. 10, the relative free-radical content in the retinal cells exposed to ultraviolet light in the first and the second embodiments is similar to that in the control group, and is significantly lower than that in the comparative embodiment. Accordingly, the aqueous solution of the emblica extract having the mass concentration of 250 μg/ml to 500 μg/ml is able to reduce the free-radical content in the retinal cells exposed to ultraviolet light, and reduce the damage to the retinal cells caused by ultraviolet light. According to the results in FIG. 3 to FIG. 8, since the aqueous solution of the emblica extract is able to protect the mitochondria in the retinal cells so as to postpone the mitochondrial breakdown, and thereby slowing down apoptosis of the retinal cells caused by the mitochondrial breakdown. Furthermore, the aqueous solution of the emblica extract is able to reduce the damage to the retinal cells due to free-radical content in the retinal cells. Accordingly, the aqueous solution of the emblica extract has positive effect on increasing cell viability of the retinal cells, so that it is apparent that the emblica extract has the effect of protecting the retinal cells, and thereby being favorable for eye care.

Put the values in Table 1 into the following formula to obtain the Bioenergetic Health Index (BHI) of the first embodiment, the second embodiment, the comparative embodiment and the control group: BHI=[(the oxygen consumption rate for ATP synthesis)×(the spare respiratory capacity in the mitochondria)]/[(the oxygen consumption rate required to compensate for the proton leakage)×(the non-mitochondrial respiration)].

According to the aforementioned formula, the BHI of the first embodiment is approximately equal to 2.31, the BHI of the second embodiment is approximately equal to 2.82, the BHI of the comparative embodiment is approximately equal to 1.03, and the BHI of the control group is approximately equal to 7.10. The BHI of the first embodiment and that of the second embodiment are greater than twice that of the comparative embodiment, which indicates that the mitochondria in the retinal cells in the first and the second embodiments are healthier and better at generating energy; therefore, it is understood that the mitochondria, treated with the emblica extract, are protected.

Moreover, the capability of the mitochondria in the retinal cells in generating energy is more resistant to surrounding environment because the treatment of emblica extract. Therefore, the retinal cells can produce a large amount of ATP for self-repair and maintain basal metabolism even though the retinal cells are under environmental stress (e.g., oxidative stress) or are damaged. When there is sufficient energy for repairing damaged DNA in the retinal cells, the retinal cells are prevented from apoptosis induced by damaged DNA. Accordingly, the use of the emblica extract includes the increase of the resistance of the retinal cells to oxidative stress and apoptosis.

According to the use of the emblica extract in preparing the pharmaceutical composition for protecting the mitochondria in the retina as described above, providing the emblica extract to the retinal cells is favorable for protecting the inner membranes of the mitochondria in the retinal cells, thereby possible to postpone the mitochondrial breakdown; furthermore, the emblica extract is able to reduce the free-radical content in the retinal cells so as to be favorable for slowing down apoptosis of the retinal cells due to breakdown of the mitochondria, and the emblica extract is also able to reduce the free-radical content in the retinal cells, thereby reducing the damage to the retinal cells due to high free-radical content. The emblica extract has the use of protecting the retinal cells so as to be favorable for eye care.

The embodiments were chosen and described in order to best explain the principles of the disclosure and its practical applications, to thereby enable others skilled in the art to best utilize the disclosure and various embodiments with various modifications as are suited to the particular use contemplated. It is intended that the scope of the disclosure be defined by the following claims and their equivalents.

What is claimed is:

1. A method for protecting mitochondria in retina cells under or exposed to ultraviolet light, comprising:
    administrating to said retina cells an effective amount of a composition containing an emblica extract, wherein said administrating results in improvement of the ability of the mitochondria in performing oxidative phosphorylation for the synthesis of the adenosine triphosphate (ATP) and improvement of coupling efficiency of the synthesis of the adenosine triphosphate by the mitochondria,
    wherein the emblica extract comprises 35-55 wt % of a mixture of Emblicanin-A and Emblicanin-B, 4-15 wt % of Punigluconin, 10-20 wt % of Pedunculagin, 5-15 wt % of Rutin and 10-30 wt % of Gallo-ellagitannoids.

2. The method according to claim 1, wherein the emblica extract has multiple characteristic infrared absorption peaks at $3403.6\pm5$ $cm^{-1}$, $2931.6\pm5$ $cm^{-1}$, $1385.0\pm5$ $cm^{-1}$, $1318.6\pm5$ $cm^{-1}$, $1623.5\pm5$ $cm^{-1}$, $1451.3\pm5$ $cm^{-1}$, $1352.1\pm5$ $cm^{-1}$, $1218.4\pm5$ $cm^{-1}$, $1148.6\pm5$ $cm^{-1}$, $1035.7\pm5$ $cm^{-1}$ and $3403.6\pm5$ $cm^{-1}$, respectively.

3. The method according to claim 1, wherein the emblica extract has multiple characteristic peaks on a high-performance liquid chromatogram at retention time of $1.620\pm0.5$ min, $2.148\pm0.5$ min, $3.265\pm0.5$ min and $4.370\pm0.5$ min, respectively.

4. The method according to claim 1, wherein the emblica extract is obtained from the fruit of *Emblica officinalis* by extraction with salt.

5. The method according to claim 1, wherein the emblica extract is provided to the retinal cells in the form of an aqueous solution of the emblica extract.

6. The method according to claim 5, wherein a mass concentration of the emblica extract in the aqueous solution is from 250 to 500 µg/ml.

7. The method according to claim 1, wherein the composition is in an oral dosage form.

8. The method according to claim 7, wherein an effective dose of the emblica extract in the composition is from 60.75 mg to 121.5 mg.

9. The method according to claim 8, wherein the composition is encapsulated in a soft capsule or a hard capsule.

10. The method according to claim 1, wherein said administrating further results in reduction of a proton leakage in the mitochondria.

11. The method according to claim 1, wherein said administrating further results in increase of a cell viability of the retinal cells.

12. The method according to claim 1, wherein said administrating further results in reduction of a production of free radical in the retinal cells.

13. The method according to claim 1, wherein said administrating further results in increase of a resistance of the retinal cells to oxidative stress.

14. The method according to claim 1, wherein said administrating further results in increase of a resistance of the retinal cells to apoptosis.

* * * * *